(12) United States Patent
Tucker et al.

(10) Patent No.: US 11,576,742 B2
(45) Date of Patent: Feb. 14, 2023

(54) CONTROLLING A SURGICAL INSTRUMENT (71) Applicant: CMR SURGICAL LIMITED, Cambridge (GB)

(72) Inventors: Edward James Wildin Tucker, Cambridge (GB); Gordon Thomas Deane, Cambridge (GB); Rachel Marie Garsed, Cambridge (GB); Rebecca Anne Cuthbertson, Cambridge (GB); Ross Hamilton Henrywood, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 471 days.

(21) Appl. No.: 16/492,729

(22) PCT Filed: Mar. 9, 2018

(86) PCT No.: PCT/GB2018/050603
§ 371 (c)(1),
(2) Date: Sep. 10, 2019

(87) PCT Pub. No.: WO2018/162921
PCT Pub. Date: Sep. 13, 2018

(65) Prior Publication Data
US 2021/0145532 A1 May 20, 2021

(30) Foreign Application Priority Data
Mar. 10, 2017 (GB) ...................................... 1703893

(51) Int. Cl.
*A61B 34/00* (2016.01)
*A61B 34/35* (2016.01)
(52) U.S. Cl.
CPC .............. *A61B 34/76* (2016.02); *A61B 34/35* (2016.02); *A61B 34/74* (2016.02)

(58) Field of Classification Search
CPC ......... A61B 34/76; A61B 34/35; A61B 34/74; A61B 34/30; A61B 34/70; A61B 34/37; A61B 2034/742; B25J 9/1689
See application file for complete search history.

(56) References Cited

U.S. PATENT DOCUMENTS 3,171,549 A * 3/1965 Orloff .................... G05G 9/047
414/6
5,792,135 A 8/1998 Madhani et al.
(Continued)

FOREIGN PATENT DOCUMENTS

| CN | 102892375 A | 1/2013 |
| CN | 103648427 A | 3/2014 |

(Continued)

OTHER PUBLICATIONS

International Search Report and the Written Opinion of the International Searching Authority from corresponding PCT/GB2018/050603 dated May 11, 2018.
(Continued)

*Primary Examiner* — Julian W Woo
(74) *Attorney, Agent, or Firm* — Lando & Anastasi, LLP (57) ABSTRACT

A control system for regulating operative control of a surgical instrument by a remote surgeon input device. The surgical instrument is supported by an articulated robot arm, and comprises an end effector connected to a shaft by an articulated coupling. The remote surgeon input device is capable of operatively controlling the surgical instrument by controlling articulation of the end effector, and controlling articulation of the robot arm and coupling. On receiving a request to engage operative control of the surgical instrument by the surgeon input device, the control system initially engages operative control of articulation of the robot arm and coupling by the surgeon input device, whilst maintaining disengagement of operative control of articula-
(Continued)

tion of the end effector by the surgeon input device. Subsequently, the control system engages operative control of articulation of the end effector by the surgeon input device following a manipulation of the surgeon input device.

14 Claims, 5 Drawing Sheets

(56) References Cited

U.S. PATENT DOCUMENTS

| | | | | |
|---|---|---|---|---|
| 6,587,750 | B2* | 7/2003 | Gerbi | A61B 34/71 600/595 |
| 6,852,107 | B2* | 2/2005 | Wang | A61B 34/35 606/1 |
| 6,879,880 | B2* | 4/2005 | Nowlin | A61B 34/70 318/568.22 |
| 9,244,523 | B2* | 1/2016 | Ogawa | A61B 34/37 |
| 2001/0018591 | A1 | 8/2001 | Brock et al. | |
| 2002/0143319 | A1 | 10/2002 | Brock | |
| 2003/0060927 | A1 | 3/2003 | Gerbi et al. | |
| 2003/0135203 | A1 | 7/2003 | Wang et al. | |
| 2010/0225209 | A1 | 9/2010 | Goldberg et al. | |
| 2010/0234857 | A1 | 9/2010 | Itkowitz et al. | |
| 2014/0094825 | A1 | 4/2014 | Flaherty et al. | |
| 2014/0148950 | A1 | 5/2014 | Ogawa et al. | |
| 2015/0272683 | A1 | 10/2015 | Yang et al. | |
| 2016/0235489 | A1 | 8/2016 | Gombert et al. | |

FOREIGN PATENT DOCUMENTS

| | | |
|---|---|---|
| CN | 103747759 A | 4/2014 |
| JP | 2005515012 A | 5/2005 |
| JP | 201334851 A | 2/2013 |
| JP | 201335117 A | 2/2013 |
| WO | 03061482 A1 | 7/2003 |
| WO | 2013018933 A1 | 2/2013 |
| WO | 2013018934 A1 | 2/2013 |
| WO | 2015163943 A1 | 10/2015 |
| WO | 2016176755 A1 | 11/2016 |

OTHER PUBLICATIONS

United Kingdom Search Report from corresponding United Kingdom Application No. GB1703893.6 dated Jul. 24, 2017.
First Indian Examination Report from corresponding Indian Application No. 201927037655 dated Jun. 1, 2021.
Japanese Notification of Reasons for Refusal from corresponding Japanese Patent Application No. 2019-549474 dated Nov. 30, 2021 [English translation attached].
Chinese Office Action from corresponding Chinese Application 201880016947.8 dated Apr. 28, 2022.

* cited by examiner

CONTROLLING A SURGICAL INSTRUMENT

CROSS-REFERENCE TO RELATED APPLICATIONS

This application is a U.S. National Phase Application under 35 U.S.C. § 371 of International Application No. PCT/GB2018/050603, filed Mar. 9, 2018, which claims priority to United Kingdom Application No. 1703893.6, filed Mar. 10, 2017. Each application referenced above is hereby incorporated by reference in its entirety for all purposes.

BACKGROUND

Figure 1:
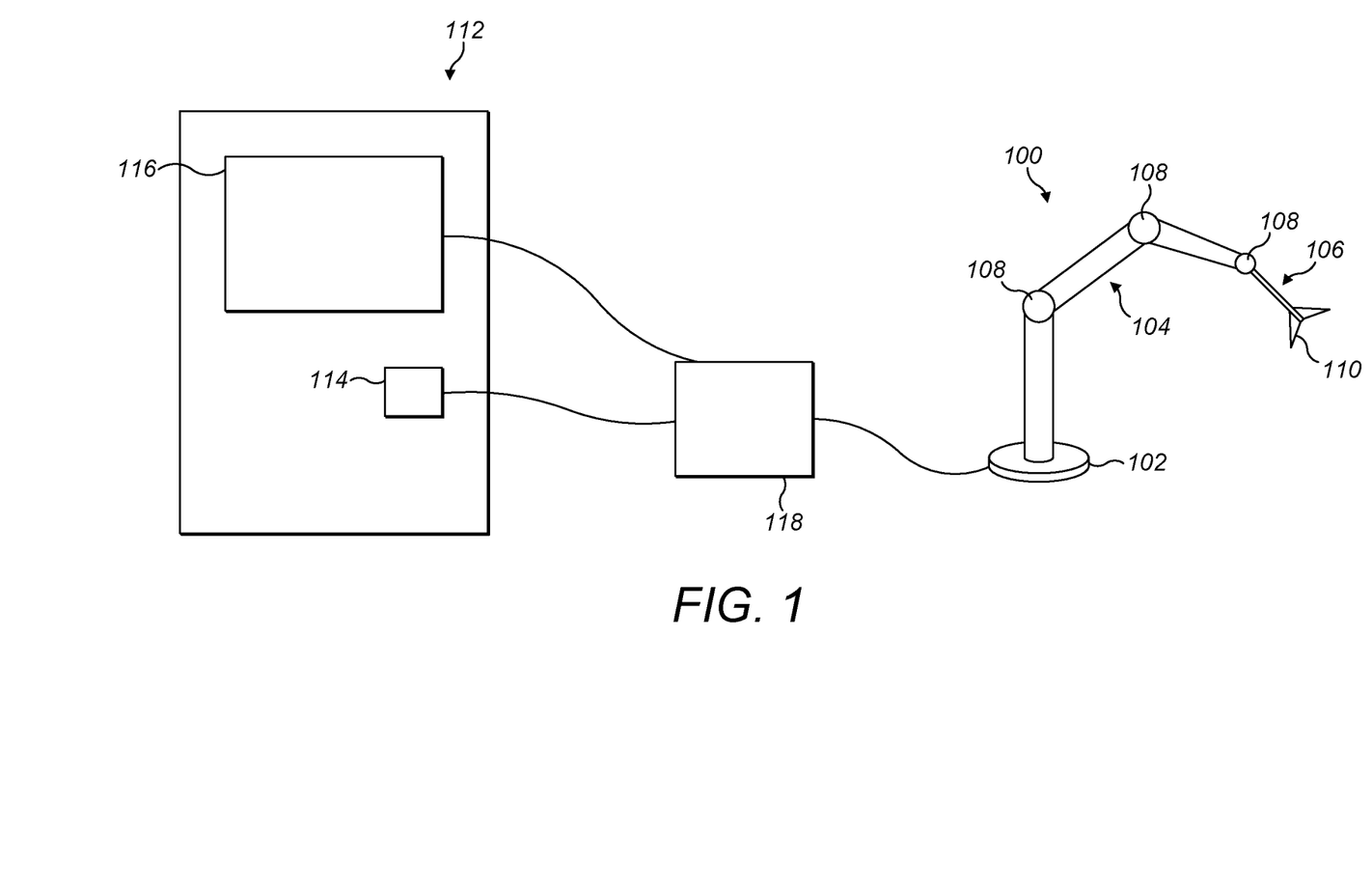
FIG. 1 illustrates a surgical robot system for performing a surgical procedure.

It is known to use robots for assisting and performing surgery. FIG. 1 illustrates a typical surgical robotic system. A surgical robot 100 consists of a base 102, an arm 104 and an instrument 106. The base supports the robot, and is itself attached rigidly to, for example, the operating theatre floor, the operating theatre ceiling or a trolley. The arm extends between the base and the instrument. The arm is articulated by means of multiple flexible joints 108 along its length, which are used to locate the surgical instrument in a desired location relative to the patient. The surgical instrument is attached to the distal end of the robot arm. The surgical instrument penetrates the body of the patient at a port so as to access the surgical site. At its distal end, the instrument comprises an end effector 110 for engaging in a surgical procedure. In FIG. 1, the illustrated end effector is a pair of jaws. A surgeon controls the surgical robot 100 via a remote surgeon console 112. The surgeon console comprises one or more surgeon input devices 114. These may take the form of a hand controller or foot pedal. The surgeon console also comprises a display 116.

A control system 118 connects the surgeon console 112 to the surgical robot 100. The control system receives inputs from the surgeon input device(s) and converts these to control signals to move the joints of the robot arm 104 and end effector 110. The control system sends these control signals to the robot, where the corresponding joints are driven accordingly. The robot may send feedback signals to the control system 118, for example force feedback as measured by force sensors on the robot arm. The control system receives the feedback signals and converts them to control signals to the surgeon console 112. For example, the control system may convert a feedback signal to a control signal to generate an image on the display 116. As another example, the control system may convert a feedback signal to a control signal to cause the surgeon input device 114 to provide a haptic indication to the surgeon. The control system may be connected to other devices, such as an endoscope. The control system controls the display 116 to display the video signal received from the endoscope.

It is known for the surgeon input device to include a clutch. The control system 118 regulates control of the robot arm in accordance with the clutch. Specifically, when the clutch is engaged, the control system 118 disengages control of the robot arm and instrument from the surgeon input device. When the clutch is disengaged, the control system 118 reengages control of the robot arm and instrument to the surgeon input device. The surgeon may engage the clutch in order to disconnect the surgeon's hand controller from operative control of the robot arm and instrument, thereby enabling the surgeon to move the hand controller to a more comfortable location (or a location with a greater range of movement) within the surgeon console. Once the surgeon has moved the hand controller to the desired position, the surgeon then disengages the clutch in order to reconnect the hand controller to the robot arm and instrument.

Figure 2:
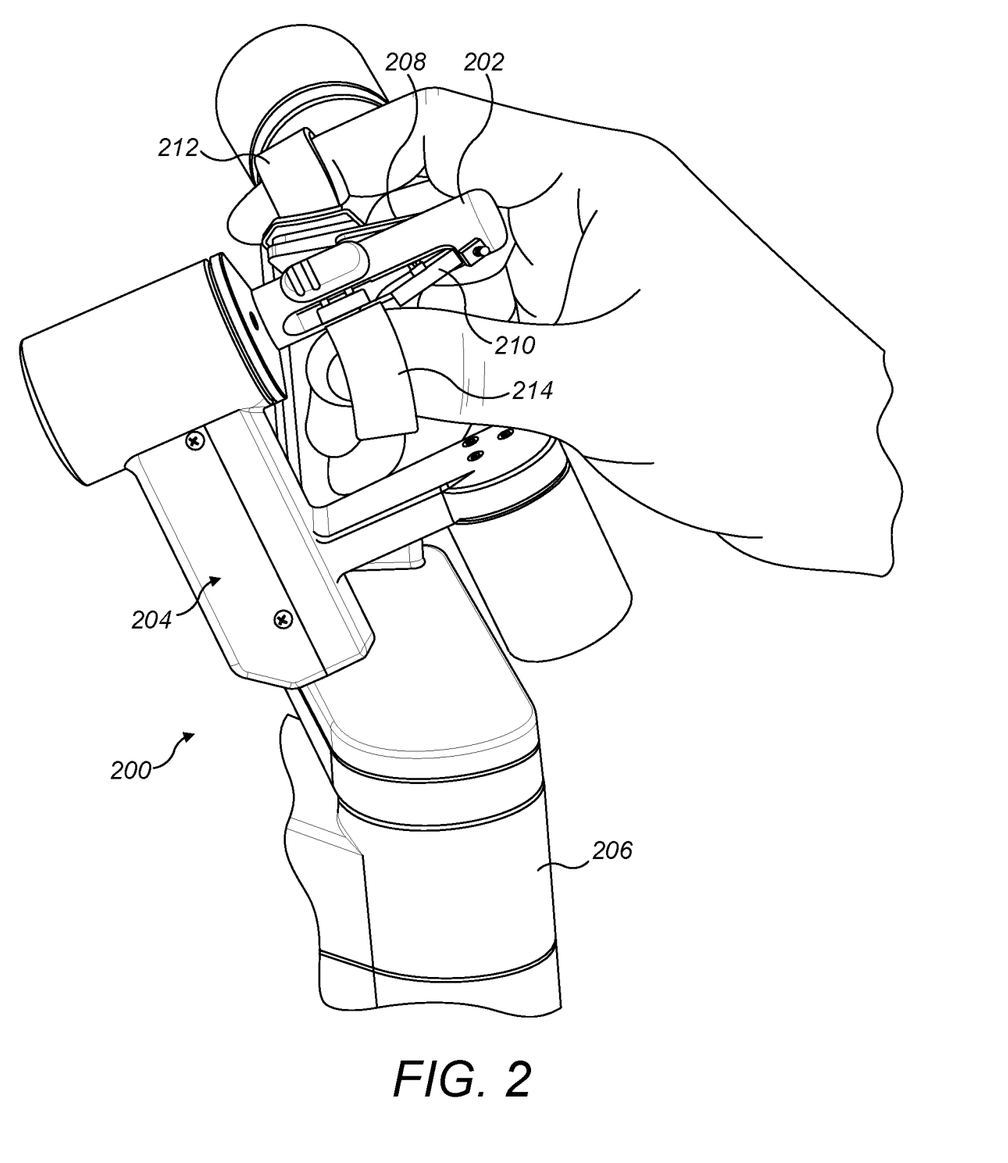
FIG. 2 illustrates a known surgeon hand controller.

FIG. 2 shows a known surgeon's hand controller 200 for manipulating an end effector that comprises a pair of movable jaws. The hand controller 200 has a primary input stem 202. The primary input stem constitutes the distal end of a gimbal system 204 which permits the primary input stem to be moved with three degrees of rotational freedom. The proximal end of the gimbal system is attached to a base by a parallelogram system, part of which is shown at 206, which permits the primary input stem to be moved with three degrees of translational freedom with respect to the base. The primary input stem is provided with two rotatable pincer elements 208, 210 which can be bound by loops 212, 214 to the surgeon's fingers. The surgeon can move the primary input stem 202 with six degrees of freedom to command a change in position of the end effector, and can move the elements 208, 210 to command opening or closing of the jaws of the end effector.

The surgeon is able to disengage/engage control of the hand controller 200 from the end effector by engaging/disengaging a foot clutch pedal (not shown). When the surgeon disengages the clutch pedal, the control system 118 sends control signals to drivers in the hand controller 200 which drive the hand controller to an orientation which matches that of the end effector of the surgical instrument. The surgeon must hold the hand controller in this orientation in order to reengage control of the end effector. The surgeon fully closes the pincer elements 208, 210. The surgeon then opens the pincer elements 208, 210. When the opening angle of the pincer elements matches the opening angle of the end effector jaws, the control system reengages total control of the robot arm and instrument to the hand controller. The reengagement is sudden, and consequently, if not well anticipated by the surgeon, may cause the end effector to move jerkily from the configuration it had during control disengagement. If the end effector jaws had been holding an object during control disengagement, then the sudden reengagement and jerky movement could cause the jaws to drop the object.

Thus, there is a need for a control system which better reengages control of the surgeon input device to the end effector following a period of disengagement.

SUMMARY OF THE INVENTION

According to an aspect of the invention there is provided a control system for regulating operative control of a surgical instrument by a remote surgeon input device, the surgical instrument being supported by an articulated robot arm, the surgical instrument comprising an end effector connected to a shaft by an articulated coupling, the remote surgeon input device capable of operatively controlling the surgical instrument by (i) controlling articulation of the end effector, and (ii) controlling articulation of the robot arm and the coupling, the control system configured to: on receiving a request to engage operative control of the surgical instrument by the surgeon input device: initially engage operative control of articulation of the robot arm and the coupling by the surgeon input device, whilst maintaining disengagement of operative control of articulation of the end effector by the surgeon input device; and subsequently engage operative control of articulation of the end effector by the surgeon input device following a manipulation of the surgeon input device.

The surgeon input device may comprise an articulated component which is manipulatable to operatively control articulation of the end effector, wherein the control system is configured to only engage operative control of the articulated component to the end effector when the articulated component is manipulated such that the configuration of the articulated component matches the configuration of the end effector.

The control system may be configured to control an actuator to drive the configuration of the articulated component towards the configuration of the end effector.

The end effector may comprise a pair of end effector elements rotatable relative to each other and separated by an end effector angle, and the articulated component of the surgeon input device may comprise a pincer element rotatable relative to another portion of the surgeon input device and separated from that other portion of the surgeon input device by a pincer angle, the pincer element for controlling rotation of the end effector elements to a separation of a drive angle, the drive angle being a function of the pincer angle. The control system may be configured to receive an indication of the end effector angle; receive an indication of the drive angle; and engage operative control of opening and closing of the end effector elements by the pincer element when the drive angle matches the end effector angle.

The control system may be configured to engage operative control of opening and closing of the end effector elements by the pincer element following: (i) opening the pincer element relative to the other portion of the surgeon input device such that the drive angle exceeds the end effector angle, and then (ii) closing the pincer element relative to the other portion of the surgeon input device until the drive angle matches the end effector angle.

The control system may only be configured to engage operative control of opening and closing of the end effector elements by the pincer element following: (i) opening the pincer element relative to the other portion of the surgeon input device to their maximum separation angle, and (ii) closing the pincer element relative to the other portion of the surgeon input device until the drive angle matches the end effector angle.

The control system may be configured to: store the end effector angle from the received indication; on receiving the request to engage operative control of the surgical instrument by the surgeon input device, periodically receive an indication of the drive angle; compare the drive angle from the most recent periodically received indication to the stored end effector angle; and determine a match when the compared drive angle is the same as the stored end effector angle.

The control system may be configured to only compare the drive angle from the most recent periodically received indication to the stored end effector angle following detection that the pincer element and other portion of the surgeon input device have been opened to their maximum separation angle.

The control system may be configured to, when the pincer element is being closed relative to the other portion of the surgeon input device, when the drive angle exceeds the end effector angle by less than a predetermined offset, control an actuator to drive the pincer element towards the other portion of the surgeon input device until the drive angle matches the end effector angle.

The drive angle may be the same as the pincer angle.

The control system may be configured to, on engaging operative control of articulation of the end effector by the surgeon input device, control the surgeon input device to generate a haptic indication to a user of the surgeon input device.

The control system may be configured to, on engaging operative control of articulation of the end effector by the surgeon input device, enable force feedback from the surgical robotic instrument to the surgeon input device.

The other portion of the surgeon input device may be a body of the surgeon input device. The other portion of the surgeon input device may be a further pincer element.

BRIEF DESCRIPTION OF THE FIGURES

The present invention will now be described by way of example with reference to the accompanying drawings. In the drawings.

DETAILED DESCRIPTION

The following describes controlling a surgical robotic instrument from a remote surgeon console. The instrument and console form part of a surgical robotic system of the type illustrated in FIG. 1.

The surgical instrument is supported by a robot arm. The robot arm is itself supported by a base. During surgery, the base is secured to part of the operating theatre, for example the floor, ceiling, trolley or patient bed. The robot arm remains at all times external to the patient. The surgical instrument attaches to the end of the robot arm distal to the base. This attachment point is external to the patient. The surgical instrument has an elongate profile, with a shaft spanning between its proximal end which attaches to the robot arm and its distal end which accesses the surgical site within the patient body. An incision is made into the patient body, through which a port is located. The surgical instrument may penetrate the patient body through the port to access the surgical site. Alternatively, the surgical instrument may penetrate the body through a natural orifice of the body to access the surgical site. At the distal end of the surgical instrument, the shaft is connected to an end effector by an articulated coupling. The end effector engages in a surgical procedure at the surgical site.

Figure 3:
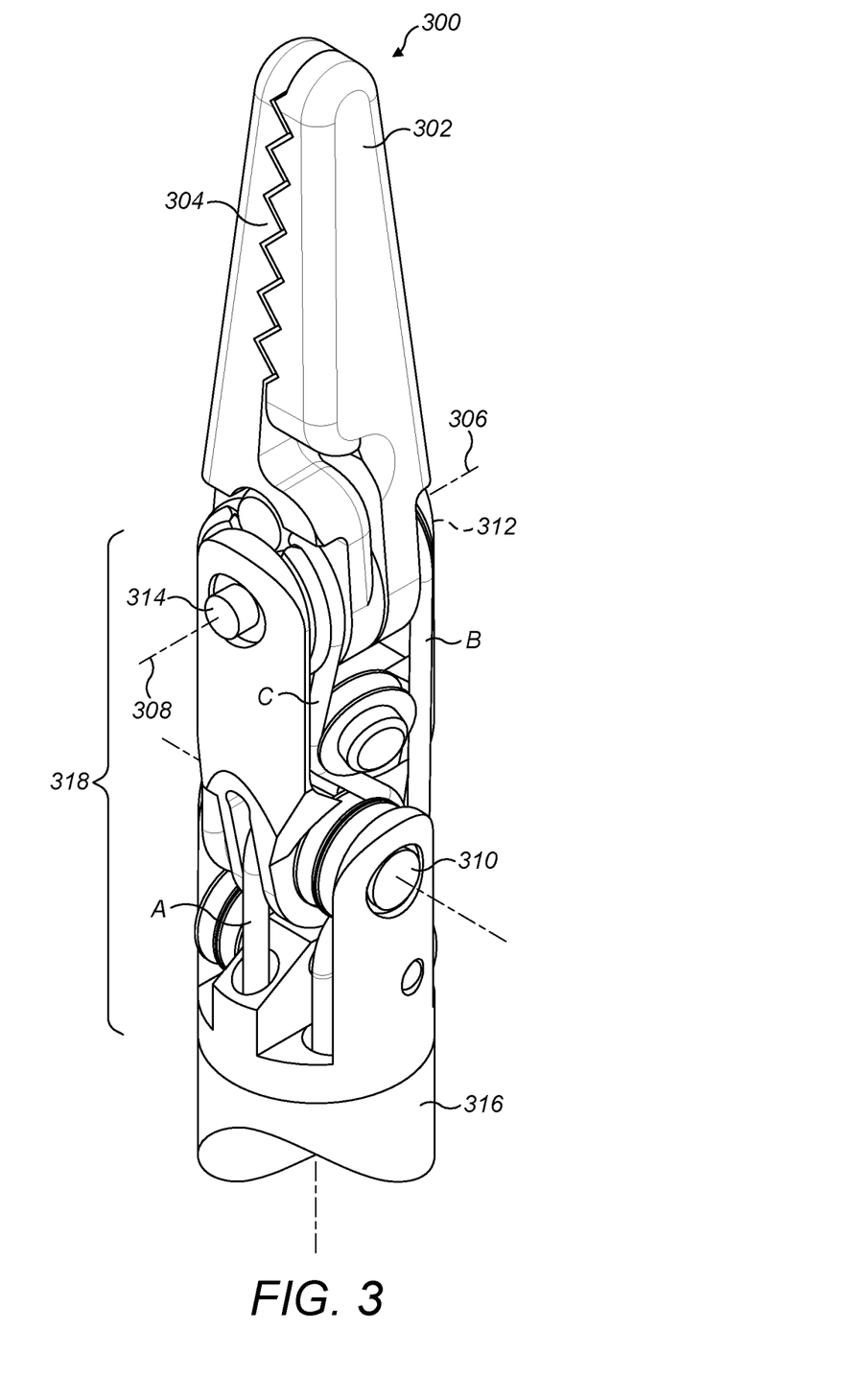
FIG. 3 illustrates the distal end of an exemplary surgical instrument.

The robot arm comprises a series of arm links interspersed with joints. These joints may be revolute joints. The distal end of the robot arm can be articulated relative to the base by movement of one or more of the joints. The proximal end of the surgical instrument and the instrument shaft may be rigid with respect to each other and rigid with respect to the distal end of the robot arm when attached to it. The articulated coupling of the surgical instrument may comprise one or more joints. This joint or joints enables the pose of the end effector to be altered relative to the direction of the instrument shaft. The end effector may also comprise joint(s). In one example, illustrated in FIG. 3, the end effector 300 is connected to the shaft 316 by articulated coupling 318. The articulated coupling 318 comprises a pitch joint 310. The end effector 300 comprises a pair of end effector elements 302, 304 (such as jaws), each of which rotates about an axis 306, 308 relative to the pitch joint 310. The joints of the articulated coupling and the end effector may be cable driven. In the example of FIG. 3, pitch joint 310 and yaw joints 312 and 314 are each independently driven by cables A, B and C respectively.

The surgical instrument can be moved at the surgical site by articulating the joints of the surgical robot arm and the articulated coupling. Separately, the surgical instrument can be moved at the surgical site by articulating the joint(s) of the end effector. Typically, during surgery, all of the surgical robot arm, articulated coupling and end effector are articulated in order to locate the end effector in the desired position and manipulate it in the desired manner. Articulating the surgical robot arm and articulated coupling in isolation causes the instrument and hence the end effector to move in translation and/or orientation. Articulating the end effector in isolation causes the pose of the end effector to change relative to the shaft of the instrument. For example, the orientation of the end effector elements may change relative to the shaft of the instrument. Articulating the end effector in isolation does not cause the end effector to move in translation. It also does not cause the orientation of the shaft of the instrument to change.

Figure 4:
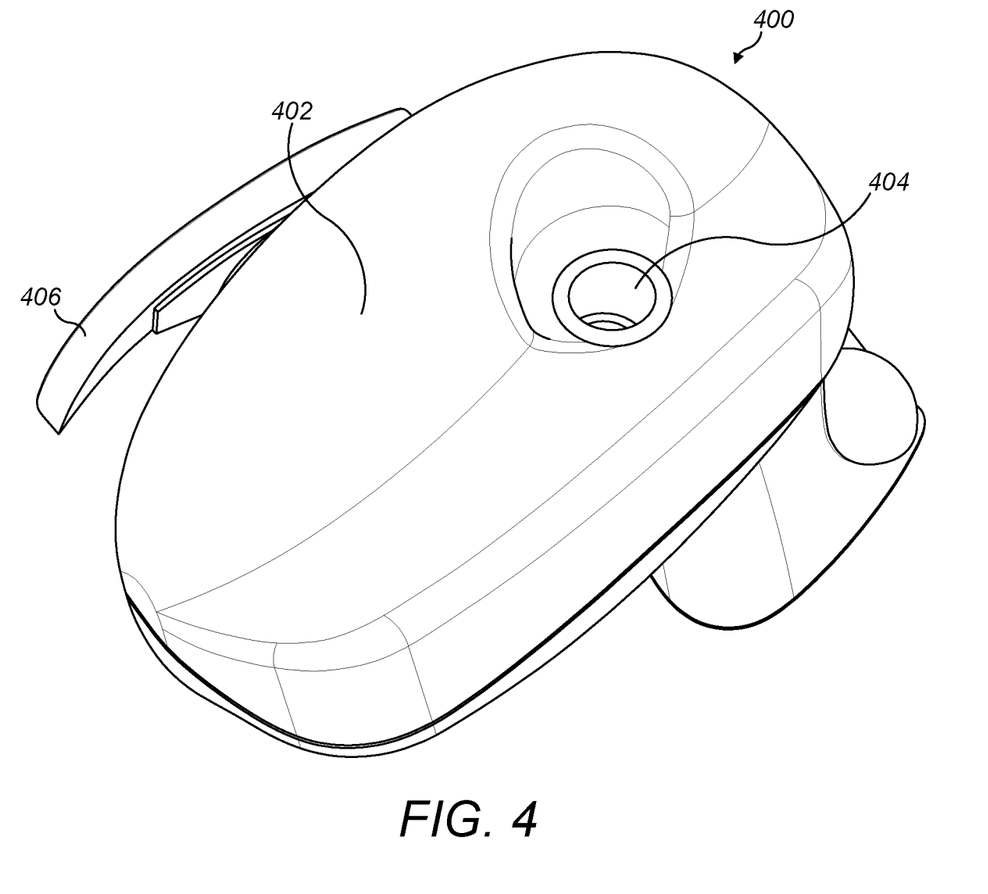
FIG. 4 illustrates an exemplary surgeon input device.

The surgeon console comprises one or more surgeon input devices. Each surgeon input device enables the surgeon to provide a control input to the control system. A surgeon input device may, for example, be a hand controller, a foot controller such as a pedal, a touch sensitive input to be controlled by a finger or another part of the body, a voice control input device, an eye control input device or a gesture control input device. The surgeon input device may provide several inputs which the surgeon can individually operate. FIG. 4 illustrates an exemplary hand controller 400. The hand controller is connected to the surgeon console, for example by a gimbal arrangement (not shown). This enables the hand controller to be moved with three degrees of translational freedom with respect to the surgeon console. The hand controller shown is intended to be held by a right hand. A mirror image hand controller could be held by a left hand. The hand controller comprises a body 402 suitable for being gripped by a hand. The hand controller may comprise additional inputs, for example buttons, switches, levers, slide inputs or track pads. The hand controller of FIG. 4 comprises a button 404 and a pincer element 406.

Different inputs from the surgeon console may control articulation of the robot arm and the articulated coupling compared to those inputs which control articulation of the end effector. Taking the hand controller of FIG. 4 as an example, translating the hand controller (without changing its orientation or operating the additional inputs on the hand controller) may control articulation of the robot arm joints only. Translating the hand controller is entirely accommodated by movement of the gimbal system. Changing the orientation of the hand controller (without translating it or operating the additional inputs on the hand controller) may control articulation of the robot arm joints and/or joint(s) of the articulated coupling. For example, rotating the hand controller may cause the whole instrument to rotate by virtue of the robot arm rotating the proximal end of the instrument. Alternatively, rotating the hand controller may cause the end effector to rotate by actuating the pitch joint 310. Changing the orientation of the hand controller is entirely accommodated by movement of the gimbal system. Actuating the additional inputs may control articulation of the end effector. For example, movement of the pincer element 406 may cause opening and closing of the jaws of an end effector.

The surgeon console may comprise a clutch input. The surgeon disengages his operative control of the surgical instrument that a surgeon input device was controlling by activating the clutch input. The surgeon reengages his operative control of the surgical instrument by deactivating the clutch input. The clutch input may be an input on the surgeon input device itself. In the example of the hand controller of FIG. 4, the clutch input may be button 404 on the hand controller. In this case, the clutch input may only be used to disengage and reengage operative control of the surgeon input device it is located on. Alternatively, the clutch input may be an input elsewhere on the surgeon console, separate to the surgeon input device. For example, the clutch input may be a foot pedal. In this case, the clutch input may be used to disengage and reengage operative control of a single surgeon input device. Alternatively, the clutch input may be used to disengage and reengage operative control of two, more or all of the surgeon input devices which the surgeon has operative control of.

A control system connects the surgeon console to the surgical robot. The control system comprises a processor and a memory. The memory stores, in a non-transient way, software code that can be executed by the processor to cause the processor to control the surgeon console and robot arm and instrument in the manner described herein. The control system receives the inputs from the surgeon input device(s) and converts these to control signals to move the joints of the robot arm and/or the joint(s) of the articulated coupling and/or the joint(s) of the end effector. The control system sends these control signals to the robot arm, where the corresponding joints are driven accordingly.

The control system regulates operative control of the surgical instrument by the surgeon input device. The control system is able to connect and disconnect the surgeon input device from operatively controlling the surgical instrument. The control system may be able to switch the device which the surgeon input device is controlling. For example, the control system may be able to switch the surgeon input device from controlling one surgical instrument supported by one robot arm to another surgical instrument supported by a different robot arm. The control system may be able to switch the surgeon input device from controlling a surgical instrument to controlling a surgical endoscope. The control system also controls the images which are displayed on the display of the surgeon console. For example, the control system may control which endoscope video feed is displayed. The control system may also control the meta data about the surgical system which is displayed.

The control system may regulate operative control of the surgical instrument by the surgeon input device such that it permits the orientation of the surgeon input device to differ from the orientation of the end effector as it appears on the display. This enables the surgeon to implement the following procedure. Firstly, the surgeon can engage the clutch, thereby disengaging control of the surgical instrument from the surgeon input device. Whilst the clutch is engaged, the surgeon can move the surgeon input device to a different position and/or orientation. Following this, the orientation of the surgeon input device does not match that of the visual orientation of the end effector on the display. For example, in the case of a hand controller, the surgeon can move the hand controller to a more comfortable position and/or orientation (or a location with a greater range of movement) within the range permitted by the console. The surgeon can then disengage the clutch, which causes control of the surgical instrument by the surgeon input device to be reengaged. The surgeon can then continue the surgical procedure.

Figure 5:
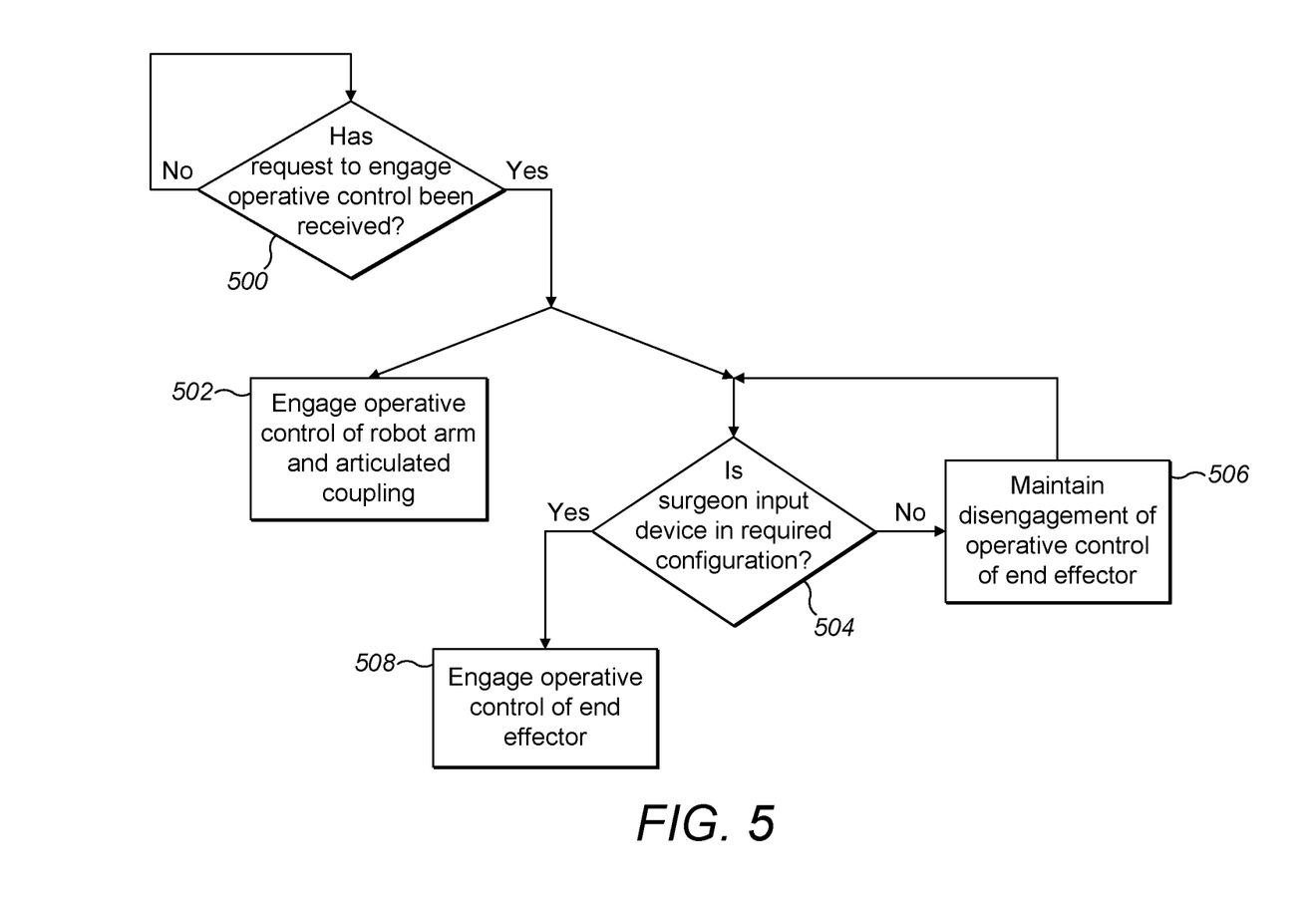
FIG. 5 is a flowchart of a method of engaging operative control of a surgical instrument by a surgeon input device.

The control system may regulate operative control of the surgical instrument by the surgeon input device as illustrated in the flowchart of FIG. 5. At step 500, the control system determines whether it has received a request to engage operative control of the surgical instrument by the surgeon input device. This request may be an input from the surgeon input device to disengage a clutch mode. This request may be an input from the surgeon input device to engage operative control of an instrument that it was not previously controlling, for example at the start of an operation or following instrument exchange. If the control system has received a request, then at step 502, the control system engages operative control of articulation of the joints of the robot arm and the articulated coupling by the surgeon input device. If the control system has received the request at step 500, then at step 504, the control system determines whether the surgeon input device is in a required configuration.

As described with respect to FIG. 4, the surgeon input device may comprise one or more inputs which the surgeon manipulates in order to control the manipulation of a particular joint or joints of the end effector. For example, the surgeon input device may comprise an articulated component which the surgeon manipulates in order to operatively control the articulation of a joint(s) of the end effector. The required configuration of the surgeon input device in step 504 may be the configuration of the surgeon input device when the configuration of the articulated component matches the configuration of the articulated end effector.

For example, consider the example that the articulated end effector is a pair of end effector elements, such as the pair of jaws shown in FIG. 3. These end effector elements are rotatable relative to each other. The end effector elements may be rotatable about a common axis. Alternatively, the end effector elements may rotate about parallel but non-coincident axes. Alternatively, the end effector elements may rotate about non-parallel axes. The longitudinal extents of the end effector elements are separated by an opening angle, referred to in the following as an end effector angle. In the configuration of FIG. 3, the jaws are closed, and hence the end effector angle is 0°. The articulated component of the surgeon input device controls the rotation of the end effector elements. The articulated component of the surgeon input device may comprise a pincer element, such as the pincer element 406 of the hand controller of FIG. 4, which is rotatable relative to another portion of the surgeon input device. The pincer element is separated from that other portion of the surgeon input device by an opening angle, referred to in the following as a pincer angle. The other portion of the surgeon input device may be the body of the surgeon input device. For example, in the hand controller of FIG. 4, the other portion of the surgeon input device is the outer surface of the body of the hand controller which is most proximal to the pincer element. Alternatively, the other portion of the surgeon input device may be another pincer element. In this case, the two pincer elements may be rotatable relative to each other about a common axis. Alternatively, the pincer elements may rotate about parallel but non-coincident axes. Alternatively, the pincer elements may rotate about non-parallel axes.

In this example, the pincer element controls rotation of the end effector elements to a separation of a drive angle. The drive angle is a function of the pincer angle. The drive angle may be the same as the pincer angle. For example, if the range of the pincer angle is the same as the range of the end effector angle, then the pincer element may control the end effector elements to open to the same angle as the pincer angle. If the range of the pincer angle is different to the range of the end effector angle (for example the hand controller pincer element opens more widely than or less widely than the end effector elements), then a transformation may be applied to map the pincer angle to a drive angle. This transformation may be linear. For example, the mapping may be such that the drive angle opens the end effector elements to the same percentage of their range of motion as the pincer angle opens the pincer element. The transformation may be non-linear. For example, as the pincer angle reaches the lower end of its range, this may be mapped to a smaller drive angle than would be determined using the linear transformation described above. This type of non-linear transformation may be used, for example, in needle driving, in order to maximise the grip force of the end effector elements on the needle.

In order to reengage operative control of opening and closing of the end effector elements by the pincer element, the pincer element of the surgeon input device may be required to be in a configuration which matches that of the end effector elements. This ensures that the surgeon is able to control the end effector elements with the full range of motion of the end effector elements after reengagement. This avoids the problem of, for example, the surgeon applying the clutch to disengage control of the surgeon input device when the end effector elements are fully open, and then disengaging the clutch to reengage control of the surgeon input device when the pincer angle is 0°. In this case, the end effector elements would still be fully open, but the surgeon would not be able to control them to close because the pincer element would already be in a fully closed configuration. By only reengaging operative control of the articulation of the joints of the end effector when the configuration of the pincer element matches the configuration of the end effector, this problem is solved.

To implement step 504, the control system may receive an indication of the end effector angle, and also receive an indication of the drive angle. The control system may receive the indication of the end effector angle prior to receiving the request from the surgeon input device to engage operative control of the instrument. For example, if step 500 is a surgeon input device requesting to disable the clutch following a period during which the surgeon had an instrument clutched, then the end effector angle of that instrument may have been received when that instrument was initially clutched. The control system stores the end effector angle from the received indication. The control system may periodically receive an indication of the drive angle. The control system may request this indication. This indication may be the drive angle itself, or the pincer angle. The control system may only start receiving an indication of the drive angle following the request to engage operative control of the instrument by the surgeon input device at step 500. The control system retrieves the stored end effector angle and compares the drive angle to the stored end effector angle. In the case that the control system has been periodically receiving an indication of the drive angle, the control system compares the drive angle of the most recently received indication to the stored end effector angle. Only when the drive angle matches the end effector angle, does the control system determine that the surgeon input device is in the required configuration. If the drive angle does not match the end effector angle, the control system determines that the surgeon input device is not in the required configuration.

The end effector angle may be determined from position measurements taken by position sensors. These position sensors may be located either (i) on each of the end effector joints, or (ii) on the driving elements of the interface between the robot arm and the instrument. The driving elements transfer drive between the robot arm and the instrument. For example, when a driving element is moved, it may apply tension to a driving cable in the instrument which causes an end effector joint to rotate. Thus, by measuring the location of the driving element within its range of motion, the position of the end effector joint it is driving can be determined. The end effector angle may be determined without any measurements being made. For example, if step 500 is a surgeon input device requesting to disable the clutch following a period during which the surgeon had the instrument clutched, the end effector angle may be taken to be the drive angle at the time the clutch was engaged. As another example, the end effector angle may be determined from the locations of the driving elements without their positions having to be measured. Since the control system controls the movement of the driving elements, the control system is able to determine the current position of a driving element from its initial position and the known movements that the driving element has made since that known initial position. The control system may determine the end effector angle by processing the endoscope image of the end effector. For example, the end effector angle may be measured from an image of the instrument at the surgical site as displayed.

The pincer angle may be determined from position measurements taken by position sensors located on the articulated component of the surgeon input device. The control system may determine the pincer angle without the position of the articulated component having to be measured. Since the control system receives inputs from movements of the surgeon input device, the control system is able to determine the current position of the articulated component from its initial position and the known movements that the articulated component has made since that known initial position.

If the surgeon input device is not in the required configuration, then at step 506, the control system maintains disengagement of operative control of articulation of the end effector by the surgeon input device. The control system then returns to step 504, where it reassesses whether the surgeon input device is in the required configuration. The control system may continually assess whether the surgeon input device is in the required configuration. Alternatively, the control system may periodically assess whether the surgeon input device is in the required configuration. In this case, the control system may wait for a predetermined interval after step 506 before moving onto step 504. If the surgeon input device is in the required configuration, then at step 508, the control system engages operative control of articulation of the end effector by the surgeon input device.

If the surgeon input device is initially not in the configuration required by step 504, then in order for the surgeon input device to be in the required configuration to cause operative control of the articulation of the end effector by the surgeon input device to be enabled, the surgeon input device is manipulated to bring it into the required configuration. This manipulation may be performed manually by the surgeon. Alternatively, or in addition, the control system may control an actuator to drive the articulated component of the surgeon input device to the required configuration. The motor driving the actuator may be located in the surgeon input device. The motor has sufficient torque to overcome resistance from the surgeon's hand on the articulated component. The control system may control an actuator to only drive the articulated component to the required configuration when the articulated component configuration is within a predetermined offset of the required configuration. For example, the control system may only initiate an actuator to drive a pincer element when the drive angle differs from the end effector angle by less than a predetermined offset. The control system then drives the pincer element until the drive angle matches the end effector angle. This aids the surgeon in the final stages of bringing the articulated component to the required configuration, which the surgeon may find more difficult to judge. Additionally, since only the final portion of the manipulation of the articulated component is driven, the rest being manual, the heat dissipated by the motor is reduced compared to a fully driven motion.

If the control system determines at step 504 that the surgeon input device is in the required configuration, then it may cause a haptic indication to be generated at the surgeon input device. This haptic indication indicates to the surgeon that operative control of articulation of the end effector is engaged. Thus, this haptic indication indicates to the surgeon that full control of the instrument (via both control of joints of the robot arm and articulated coupling and control of joint(s) of the end effector) is engaged. The haptic feedback may be any one or more of the following: a click, detent or rumble (vibration) provided by a motor. This motor may be located in the surgeon input device. The control system may cause an audible indication to be generated at the surgeon console to indicate that the surgeon input device is in the required configuration. The control system may cause a visual indication to be generated at the surgeon console, for example on the display, to indicate that the surgeon input device is in the required configuration.

If the control system determines at step 504 that the surgeon input device is in the required configuration, then it may enable a force feedback loop from the instrument to the surgeon input device. The force feedback provides the surgeon with a sensation which is related to the engagement between the end effector and its surroundings at the surgical site. The control system receives measurements from force sensors on the robot arm joints, from which it determines forces applied to the instrument. Thus, the control system causes a motor to move the surgeon input device in a manner that the surgeon is able to feel but that does not impede his actions. This movement indicates to the surgeon the forces applied to the instrument. Thus, the surgeon has a sensation, for example of grasping and manipulating tissue, through the force feedback.

In the flowchart of FIG. 5, the control system reengages operative control of the end effector to the surgeon input device when the surgeon input device has a required configuration. The control system may require the surgeon input device to have been manipulated to the required configuration in a particular manner. Taking the end effector elements of FIG. 3 and the pincer element of FIG. 4 as an example, the control system may require the surgeon input device to be manipulated such that the pincer element is opened relative to the other portion of the surgeon input device such that the drive angle exceeds the end effector angle, and then the pincer element closed relative to the other portion of the surgeon input device until the drive angle matches the end effector angle. When the drive angle matches the end effector angle, the control system determines that the surgeon input device is in the required configuration, and engages operative control of the end effector by the surgeon input device. By requiring the pincer element to be opened such that the drive angle exceeds the end effector angle, the control system ensures that operative control of the end effector is initiated whilst the surgeon is closing the pincer element. Thus, when operative control is initiated, the end effector elements will begin to close. This ensures that, if the end effector elements had been holding an object whilst the surgeon's operative control was disengaged, upon reengaging the surgeon's operative control, the object will not be dropped.

In order for the surgeon's operative control of the end effector to be engaged, the control system may require that the pincer element is first opened relative to the other portion of the surgeon input device such that the drive angle is at its maximum. For example, this may be when the pincer element is opened relative to the other portion of the surgeon input device to their maximum separation angle. Then, on closing the pincer element relative to the other portion of the surgeon input device, the surgeon's operative control of the end effector is engaged when the drive angle matches the end effector angle. This ensures that, for any end effector angle, the surgeon has opened the pincer element such that the drive angle exceeds the end effector angle.

The control system may only start to compare the drive angle to the end effector angle once the drive angle is at its maximum. For example, the control system may only start to compare the drive angle to the end effector angle once it has determined that the pincer element has been opened relative to the other portion of the surgeon input device to their maximum separation angle. This ensures that the control system does not determine that the surgeon input device is in the required configuration (and hence reengage the surgeon's operative control of the end effector) if the drive angle matches the end effector angle as the surgeon opens the pincer element relative to the other portion of the surgeon input device.

If the control system controls an actuator to drive the pincer element towards the required configuration, the control system may only take this action if the drive angle exceeds the end effector angle. The control system may only take this action once the drive angle maximum has been reached.

A surgeon may utilise the methods described herein to purposefully enable control of the robot arm whilst disabling control of the end effector. This may be of use, for example, whilst the surgeon is moving the instrument from one location at the surgical site to another location at the surgical site. During this motion, he may want the end effector to remain in one configuration, for example he may want the jaws to remain closed. By clutching out the surgeon input device and then clutching back in with the pincer element open, the surgeon ensures that he only has control of the robot arm and the articulated coupling. Thus, he will not inadvertently change the configuration of the end effector as he translates the instrument to another location at the surgical site. Once the surgeon is ready to reengage his control of the end effector, he can manually manipulate the surgeon input device as described above to the required configuration to cause the control system to reengage his control of the end effector.

The robot described herein could be for purposes other than surgery. For example, the port could be an inspection port in a manufactured article such as a car engine and the robot could control a viewing tool for viewing inside the engine.

The end effector may take any suitable form. For example, the end effector could be a pair of scissors, a blade, pincers, jaws, serrated jaws, stapler, needle driver or a cauteriser.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A control system configured to regulate operative control of a surgical instrument by a remote surgeon input device, the surgical instrument being supported by an articulated robot arm, the surgical instrument comprising an end effector connected to a shaft by an articulated coupling, the remote surgeon input device capable of operatively controlling the surgical instrument by (i) controlling articulation of the end effector, and (ii) controlling articulation of the robot arm and the coupling, the control system comprising a processor and a memory, wherein the control system is configured to:
    on receiving a request to engage operative control of the surgical instrument by the surgeon input device:
    initially engage operative control of articulation of the robot arm and the coupling by the surgeon input device, whilst maintaining disengagement of operative control of articulation of the end effector by the surgeon input device, such that inputs received from the surgeon input device can cause articulation of the robot arm and the coupling but cannot cause articulation of the end effector; and
    subsequently engage operative control of articulation of the end effector by the surgeon input device following a manipulation of the surgeon input device to a required configuration.

2. A control system as claimed in claim 1, wherein the surgeon input device comprises an articulated component which is manipulatable to operatively control articulation of the end effector, wherein the control system is configured to only engage operative control of the articulated component to the end effector when the articulated component is manipulated such that the configuration of the articulated component matches the configuration of the end effector.

3. A control system as claimed in claim 2, configured to control an actuator to drive the configuration of the articulated component towards the configuration of the end effector.

4. A control system as claimed in claim 2, wherein the end effector comprises a pair of end effector elements rotatable relative to each other and separated by an end effector angle, and the articulated component of the surgeon input device comprises a pincer element rotatable relative to another portion of the surgeon input device and separated from that other portion of the surgeon input device by a pincer angle, the pincer element configured to control rotation of the end effector elements to a separation of a drive angle, the drive angle being a function of the pincer angle, the control system configured to:
    receive an indication of the end effector angle;
    receive an indication of the drive angle; and
    engage operative control of opening and closing of the end effector elements by the pincer element when the drive angle matches the end effector angle.

5. A control system as claimed in claim 4, wherein the control system is configured to engage operative control of opening and closing of the end effector elements by the pincer element following:
  (i) opening the pincer element relative to the other portion of the surgeon input device such that the drive angle exceeds the end effector angle, and then
  (ii) closing the pincer element relative to the other portion of the surgeon input device until the drive angle matches the end effector angle.

6. A control system as claimed in claim 5, only configured to engage operative control of opening and closing of the end effector elements by the pincer element following: (i) opening the pincer element relative to the other portion of the surgeon input device to their maximum separation angle, and (ii) closing the pincer element relative to the other portion of the surgeon input device until the drive angle matches the end effector angle.

7. A control system as claimed in claim 6, configured to:
  store the end effector angle from the received indication;
  on receiving the request to engage operative control of the surgical instrument by the surgeon input device, periodically receive an indication of the drive angle;
  compare the drive angle from the most recent periodically received indication to the stored end effector angle; and
  determine a match when the compared drive angle is the same as the stored end effector angle.

8. A control system as claimed in claim 7, configured to only compare the drive angle from the most recent periodically received indication to the stored end effector angle following detection that the pincer element and other portion of the surgeon input device have been opened to their maximum separation angle.

9. A control system as claimed in claim 5, configured to, when the pincer element is being closed relative to the other portion of the surgeon input device, when the drive angle exceeds the end effector angle by less than a predetermined offset, control an actuator to drive the pincer element towards the other portion of the surgeon input device until the drive angle matches the end effector angle.

10. A control system as claimed in claim 4, wherein the drive angle is the pincer angle.

11. A control system as claimed in claim 4, wherein the other portion of the surgeon input device is a body of the surgeon input device.

12. A control system as claimed in claim 4, wherein the other portion of the surgeon input device is a further pincer element.

13. A control system as claimed in claim 1, configured to, on engaging operative control of articulation of the end effector by the surgeon input device, control the surgeon input device to generate a haptic indication to a user of the surgeon input device.

14. A control system as claimed in claim 1, configured to, on engaging operative control of articulation of the end effector by the surgeon input device, enable force feedback from the surgical robotic instrument to the surgeon input device.

* * * * *